(12) United States Patent
Cha

(10) Patent No.: US 11,241,588 B2
(45) Date of Patent: Feb. 8, 2022

(54) LIGHT IRRADIATING TOOTHBRUSH HAVING MULTIPLE LIGHT SOURCES ARRANGED IN ALTERNATION

(71) Applicant: Hee Chan Cha, Seoul (KR)

(72) Inventor: Hee Chan Cha, Seoul (KR)

( * ) Notice: Subject to any disclaimer, the term of this patent is extended or adjusted under 35 U.S.C. 154(b) by 0 days.

(21) Appl. No.: 16/400,883

(22) Filed: May 1, 2019

(65) Prior Publication Data

US 2019/0255351 A1 Aug. 22, 2019

Related U.S. Application Data

(63) Continuation of application No. 14/646,397, filed as application No. PCT/KR2013/005355 on Jun. 18, 2013, now abandoned.

(30) Foreign Application Priority Data

Nov. 21, 2012 (KR) .......................... 10-2012-0132261

(51) Int. Cl.
*A61N 5/06* (2006.01)
*A46B 9/04* (2006.01)
(Continued)

(52) U.S. Cl.
CPC .............. *A61N 5/0624* (2013.01); *A46B 9/04* (2013.01); *A46B 9/06* (2013.01); *A46B 15/0036* (2013.01); *A46D 1/0207* (2013.01); *A61C 17/225* (2013.01); *A61H 13/00* (2013.01); *A61N 5/0603* (2013.01); *A46B 2200/1026* (2013.01); *A46B 2200/1066* (2013.01); *A61C 17/3481* (2013.01); *A61H 2201/0153* (2013.01); *A61H 2201/10* (2013.01); *A61H 2201/1207* (2013.01); *A61H 2201/1657* (2013.01); *A61N 5/067* (2021.08); *A61N 2005/063* (2013.01); *A61N 2005/0606* (2013.01); *A61N 2005/0644* (2013.01); *A61N 2005/0652* (2013.01); *A61N 2005/0662* (2013.01)

(58) Field of Classification Search
CPC ...... A61N 5/0624; A61N 5/0603; A46B 9/04; A46B 9/06; A46B 15/0036; A46B 15/0002; A46B 5/0095; A61C 17/225; A61C 1/0046; A61C 17/3481; A61H 13/00; A46D 1/0207
USPC ......... 15/22.1, 105, 110, 167.1; 433/29, 216
See application file for complete search history.

(56) References Cited

U.S. PATENT DOCUMENTS

| | | | |
|---|---|---|---|
| 5,836,033 A * | 11/1998 | Berge ...................... | A46B 9/06 15/110 |
| 7,269,873 B2 * | 9/2007 | Brewer .............. | A46B 15/0002 15/22.1 |

(Continued)

*Primary Examiner* — Katina N. Henson

(57) ABSTRACT

Provided is a light irradiated toothbrush, in which light sources, irradiating light having mutually different wavelengths, are arranged in alternation at the bottom of waveguide bristles so that light of different wavelengths give rise to constructive interference which strengthens the intensity of the irradiated light, and the height of the light sources are varied on the basis of the wavelength of the light irradiated therefrom so as to effectively transmit light of short wavelengths to the waveguide bristles, and light having mutually different wavelengths are transmitted by means of the waveguide bristles, thereby effectively transmitting the light to the mouth of a user.

18 Claims, 5 Drawing Sheets

(51) Int. Cl.
  *A46B 9/06*    (2006.01)
  *A46B 15/00*   (2006.01)
  *A46D 1/00*    (2006.01)
  *A61C 17/22*   (2006.01)
  *A61H 13/00*   (2006.01)
  A61C 17/34     (2006.01)
  A61N 5/067     (2006.01)

(56) References Cited

U.S. PATENT DOCUMENTS

| | | | | |
|---|---|---|---|---|
| 7,942,667 B2 * | 5/2011 | Rizoiu | ................... | A46B 5/002 |
| | | | | 15/167.1 |
| 2005/0271997 A1 * | 12/2005 | Mikami | ............. | A46B 15/0002 |
| | | | | 433/29 |
| 2006/0183071 A1 * | 8/2006 | Hsuch | .................. | A61C 19/002 |
| | | | | 433/29 |
| 2008/0286713 A1 * | 11/2008 | Nanda | ................ | A46B 15/0002 |
| | | | | 433/29 |
| 2009/0083924 A1 * | 4/2009 | Shepherd | ............. | A46B 5/0095 |
| | | | | 15/105 |
| 2011/0047729 A1 * | 3/2011 | Iwahori | ............. | A61C 17/3481 |
| | | | | 15/22.1 |
| 2013/0117950 A1 * | 5/2013 | Kim | .................... | A61C 17/221 |
| | | | | 15/22.1 |

* cited by examiner

LIGHT IRRADIATING TOOTHBRUSH HAVING MULTIPLE LIGHT SOURCES ARRANGED IN ALTERNATION

CROSS REFERENCE TO RELATED APPLICATIONS

This application is a continuation of co-pending application U.S. Ser. No. 14/646,397, filed May 21, 2015, which is the U.S. national stage application of International patent application no. PCT/KR2013/005355, filed Jun. 18, 2013.

TECHNICAL FIELD

The present invention generally relates to a vibrating toothbrush and, more particularly, to a vibrating toothbrush including light sources for emitting light.

BACKGROUND ART

As a method of removing oral bacteria that causes plaque and tartar to keep teeth sanitary, people generally brush their teeth with a toothbrush or gargle with a liquid containing a chemical antibacterial agent after brushing.

Among various types of toothbrushes, there are vibrating toothbrushes for effectively brushing teeth. Further, since it is difficult to effectively remove bacteria by brushing teeth with common toothbrushes, vibrating toothbrushes that radiate light at a predetermined wavelength band have been proposed.

However, a chemical method using mouthwash is generally used and conventional vibrating toothbrushes using light radiate only white light, so a detailed method of effectively removing oral bacteria has not been proposed yet.

DISCLOSURE

Technical Problem

Accordingly, the present invention has been made keeping in mind the above problems occurring in the related art, and the present invention is intended to propose a light irradiating toothbrush that efficiently radiates light into the mouth of a user.

Technical Solution

In order to achieve the above object, according to one aspect of the present invention, there is provided a light irradiating toothbrush including a grip and a head, in which the head includes: brushing bristles made of at least one waveguide; and a light source unit disposed under the brushing bristles inside the head and including a plurality of light sources radiating light through the waveguides, and the light source unit includes a plurality of alternatively arranged light sources radiating light with different wavelengths.

The plurality of light sources may be a set of light sources including a first sub-set that includes at least one first light source radiating short-wavelength light, and a second sub-set that includes at least one second light source radiating long-wavelength light, and the plurality of light sources may be alternately arranged by repeatedly arranging sets of light sources including the first sub-set and the second sub-set.

The short-wavelength light may be blue light and the long-wavelength light may be red light.

The light sources may be arranged in the longitudinal direction of the head.

The light sources may be LEDs (Light-Emitting Diode) or laser diodes.

The light sources may be spaced at difference distances from the brushing bristles in accordance with the magnitudes of the wavelengths, and a first light source radiating short-wavelength light may be positioned such that the short-wavelength light radiated from the first light source travels a shorter distance to the brushing bristles, as compared with long-wavelength light radiated from a second light source and traveling to the brushing bristles.

The first light source radiating short-wavelength light may be positioned closer to the brushing bristles than the second light source radiating long-wavelength light.

The brushing bristles made of waveguides may be brushing bristles made of optical fibers.

The toothbrush may further include a substrate where the light sources are disposed, and the substrate may have a white color.

The light irradiating toothbrush may further include a vibrating motor, the substrate may be composed of a first substrate and a second substrate, the first substrate may be disposed in the grip, the second substrate may be disposed in the head, the light source unit may be disposed on the second substrate, the vibrating motor may be connected to the second substrate, and the vibrating motor may vibrate the second substrate.

The light irradiating toothbrush may further include a vibration attenuator at a joint of the first substrate and the second substrate and the vibration attenuator may be made of a urethane material.

The head may further include massaging bristles made of waveguides and the massaging bristles may be formed by a bundle of a plurality of waveguides or a plurality of optical fibers.

Both or any one of the brushing bristles and the massaging bristles may be disposed on a bristle plate, and the bristle plate may be detachably attached to the head.

The brushing bristles may be coated with a metallic oxide catalyst or nano-metal, the metallic oxide catalyst may be any one of $TiO_2$, $MnO_2$, and $BaTiO_3$, or a mixture of two or more of them, and the nano-metal may be any one of nano-silver (Ag), nano-white gold (Pt), and nano-gold (Au), or a mixture of two or more of them.

The light irradiating toothbrush may be supplied with power from a battery or through a USB.

Advantageous Effects

According to the light irradiating toothbrush of an embodiment of the present invention, light sources radiating light with different wavelengths are alternately disposed under brushing bristles made of waveguides, so the intensity of light is increased by constructive interference of the light. The heights of the light sources are different in accordance with the wavelength of the light that they radiate so that short-wavelength light is transmitted well to the brushing bristles made of waveguides and light with different wavelengths is transmitted through the brushing bristles made of waveguides. Accordingly, light can be efficiently transmitted into the mouth of a user. Further, since the light irradiating toothbrush according to an embodiment of the present invention further includes a vibrating attenuator, it is possible to reduce the intensity, of vibration transmitted from a vibrating motor to the grip.

MODE FOR INVENTION

The present invention may be modified in various ways by various embodiments, and the embodiments provided are merely examples for describing the present invention in detail.

The present invention, however, is not limited to the embodiments and should be construed as including all of modifications and equivalents within the spirit and scope of the present invention.

Terms used in the specification, 'first', 'second', etc., may be used to describe various components, but the components are not to be construed as being limited to the terms. The terms are used to distinguish one component from another component. For example, the ' first' component may be named the 'second' component, and vice versa, without departing from the scope of the present invention. The term 'and/or' includes a combination of a plurality of items or any one of a plurality of terms.

It is to be understood that when one element is referred to as being "connected to" or "coupled to" another element, it may be connected directly to or coupled directly to another element or be connected to or coupled to another element, having the other element intervening therebetween. On the other hand, it is to be understood that when one element is referred to as being "connected directly to" or "coupled directly to" another element, it may be connected to or coupled to another element without the other element intervening therebetween.

Terms used in the present specification are used only in order to describe specific exemplary embodiments rather than limiting the present invention. As used herein, the singular forms are intended to include the plural forms as well, unless the context clearly indicates otherwise. It will be further understood that the terms "comprises" or "have" used in this specification, specify the presence of stated features, numerals, steps, operations, components, parts, or a combination thereof, but do not preclude the presence or addition of one or more other features, numerals, steps, operations, components, parts, or a combination thereof.

Unless indicated otherwise, it is to be understood that all the terms used in the specification including technical and scientific terms have the same meaning as those that are understood by those who skilled in the art. It must be understood that the terms defined by a dictionary are identical with the meanings within the context of the related art, and they should not be ideally or excessively formally defined unless the context clearly dictates otherwise.

Figure 1:
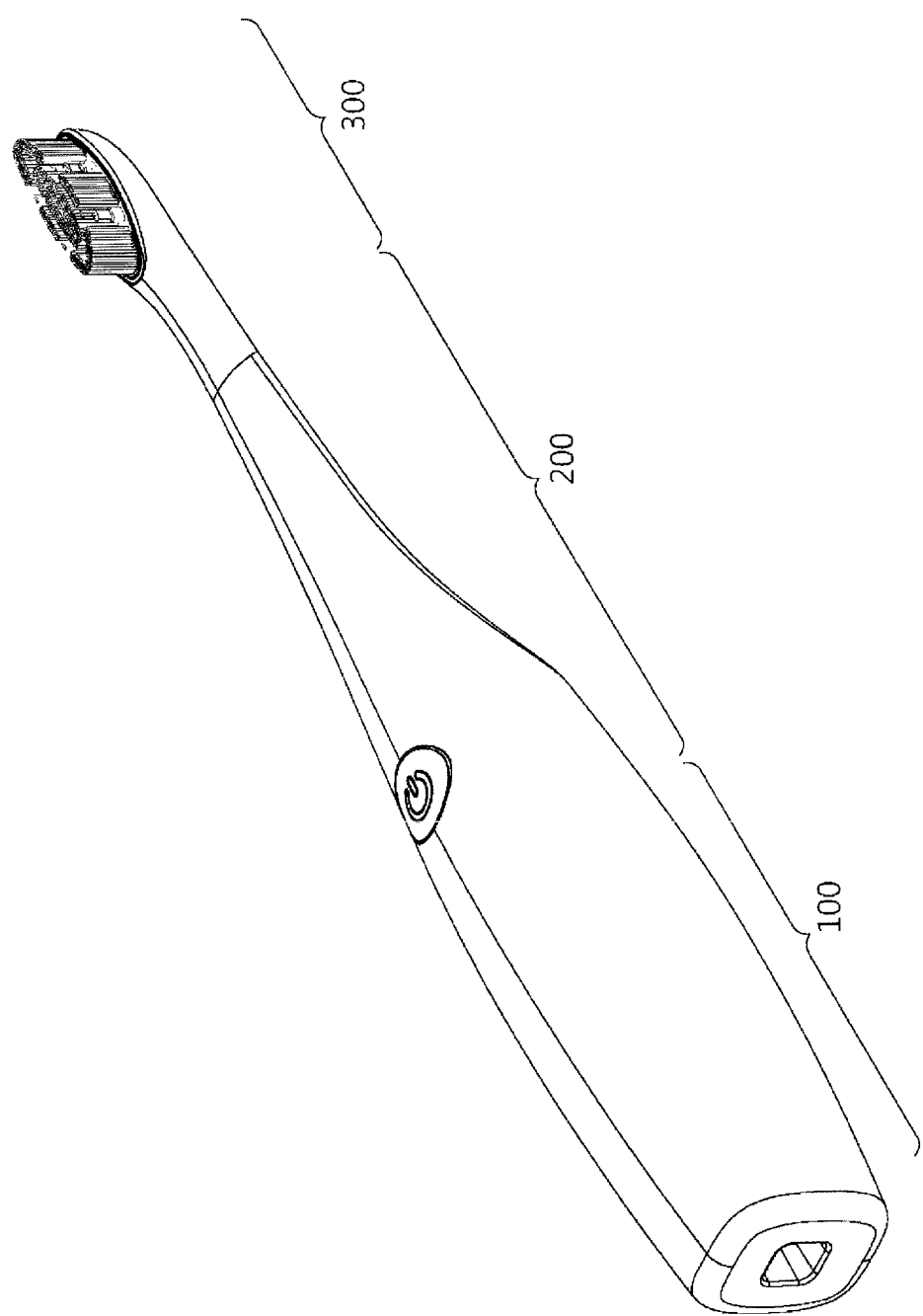
FIG. 1 is a perspective view showing the external shape of a light irradiating toothbrush according to an embodiment of the present invention.

FIG. 1 is a perspective view showing the external shape of a light irradiating toothbrush according to an embodiment of the present invention. The light irradiating toothbrush according to an embodiment of the present invention has a grip 10, a shank 200, and a head 300. The grip 100, which is the part that a user holds, includes a power button. The head 300 includes brushing bristles 310 and massaging bristles that are waveguides, and a light source unit 320, and light from light sources is transmitted to the teeth or gums of a user through the brushing bristles 310. The shank 200 connects the grip 100 and the head 300 to each other.

Figure 2:
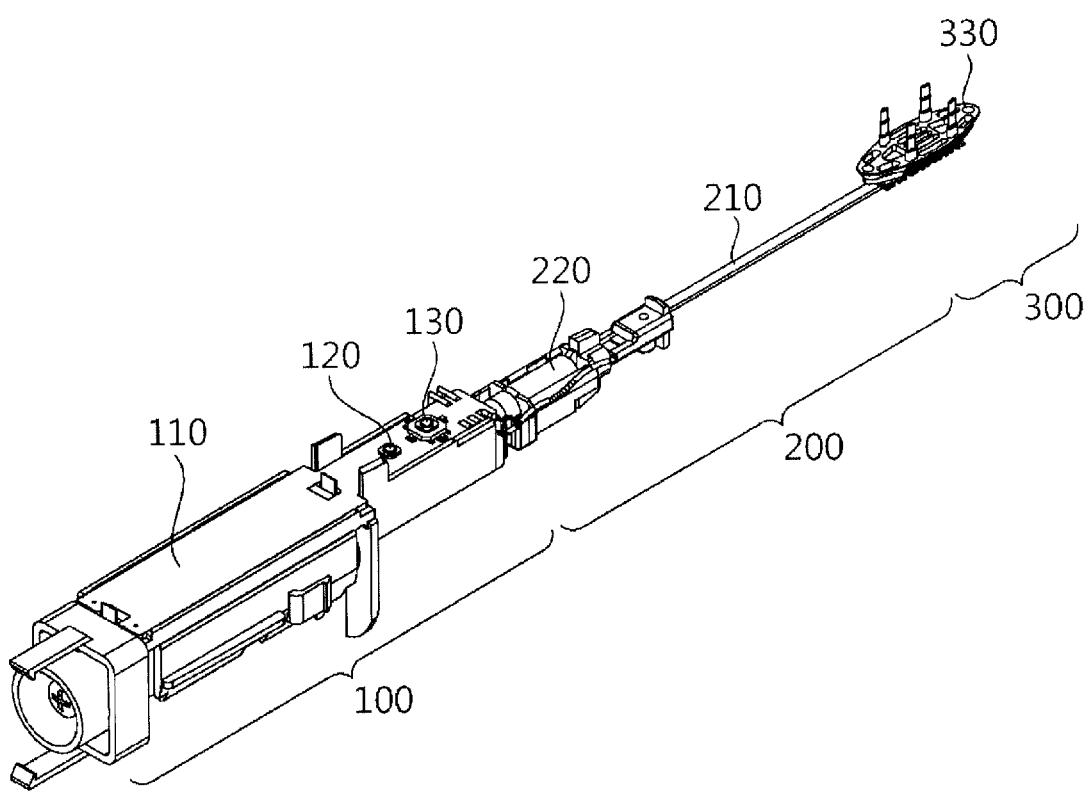
FIG. 2 is a perspective view showing the internal structure of the light irradiating toothbrush according to an embodiment of the present invention.

FIG. 2 is a perspective view showing the internal structure of the light irradiating toothbrush according to an embodiment of the present invention. The internal structure of the light irradiating toothbrush according to an embodiment of the present invention is described with reference to FIG. 2. The grip 100 includes a first substrate 110, a first housing 140, a power unit (not shown), an operation light 120, and a power switch 130. The shank 200 includes an electric motor, a second substrate 210, a second housing 240, and a vibration attenuator 230. The head 300 includes the brushing bristles 310, the massaging bristles 311, the bristle plate 330, and the light source unit 320 connected to the second substrate 210.

The first substrate and the first housing 140 may be combined. The first housing 140 and the second housing 240 may be combined through a coupler and the coupler may be the vibration attenuator 230. A vibrating motor 220 is disposed inside the second housing 240 and the second housing 240 is connected to the second substrate 210. The light source unit 320 is on an end portion of the second substrate 210. The inside of the light irradiating toothbrush according to an embodiment of the present invention is disposed in a body 500.

The configuration of the grip 100 is described. The power unit supplies power to the light irradiating toothbrush according to an embodiment of the present invention. The power unit supplies power to the vibrating motor 220 and the light source unit 320. The power unit may be disposed inside a space defined by the first substrate 110 and the first housing 140. Further, the grip 100 may include a controller (not shown) to control the light irradiating toothbrush according to an embodiment of the present invention and the controller may also be disposed in the space defined by the first substrate 110 and the first housing 140. The controller may be disposed on the first substrate 110.

The first substrate 110 may further include the operation light 120 that indicates operation of the light irradiating toothbrush according to an embodiment of the present invention and the power switch 130 that allows a user to operate the light irradiating toothbrush according to an embodiment of the present invention.

The configuration of the shank 200 is described. The vibrating motor 220 vibrates the light irradiating toothbrush according to an embodiment of the present invention so that the light irradiating toothbrush according to an embodiment of the present invention can work as a vibrating toothbrush. The vibrating motor 220 will be described in detail below.

Figure 3:
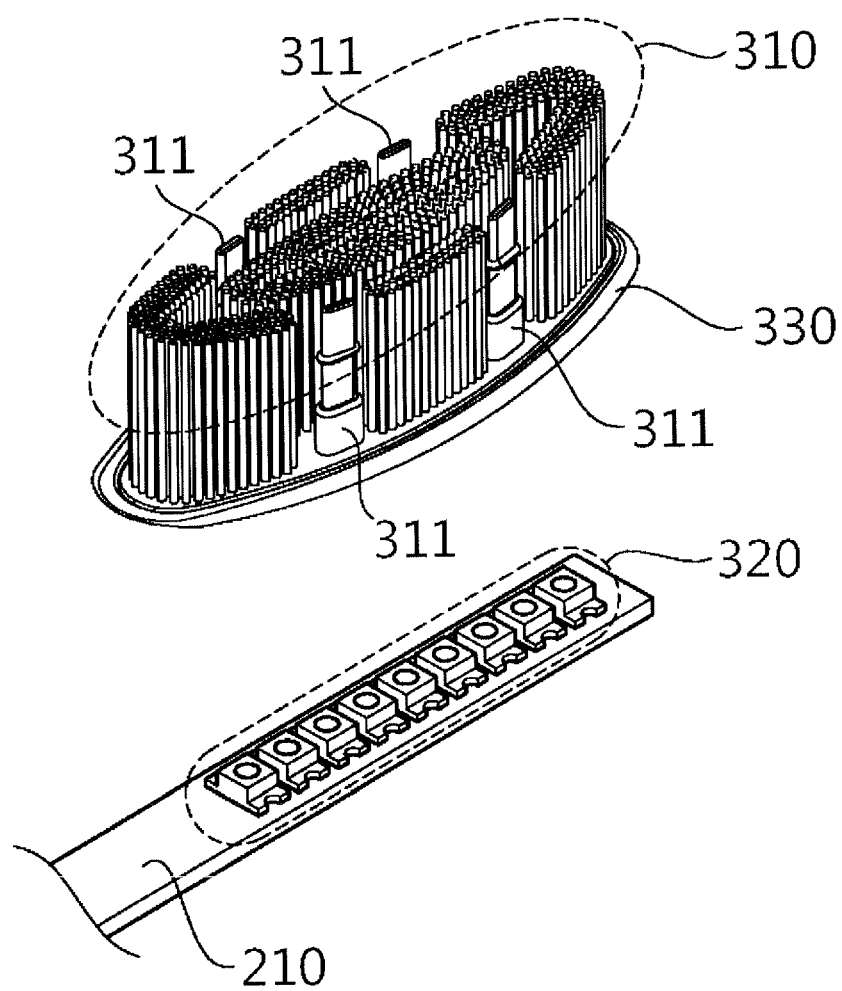
FIG. 3 is a view showing the positional relationship of brushing bristles, massaging bristles, bristle plate, and a light source unit on the head of the light irradiating toothbrush according to an embodiment of the present invention.
Figure 4:
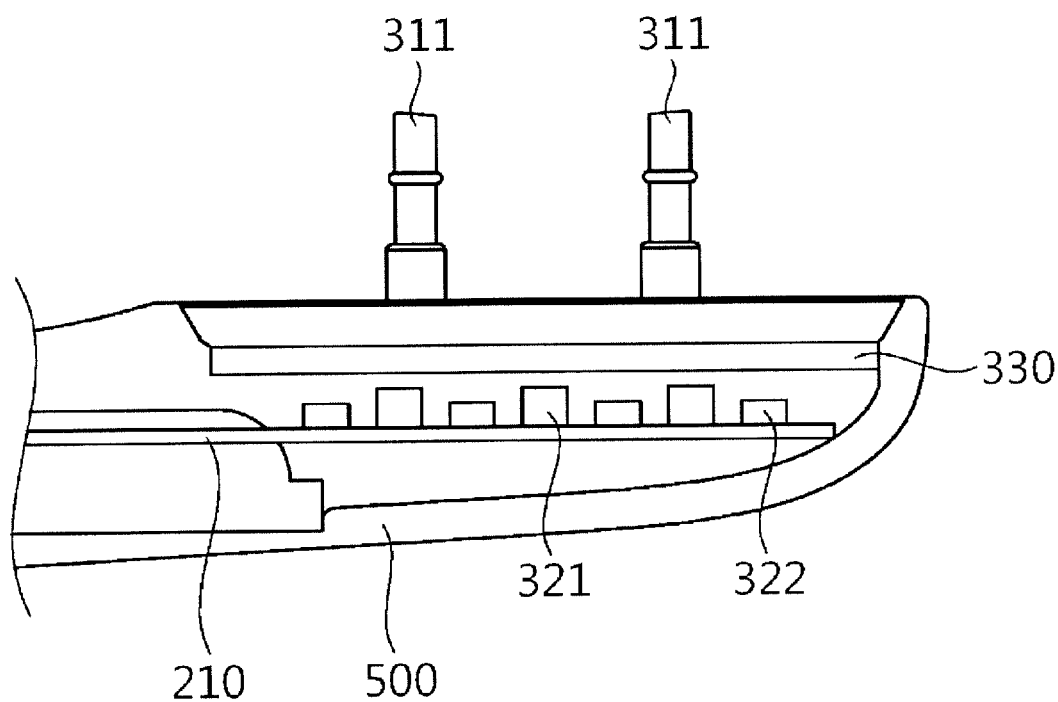
FIG. 4 is a front view showing a case when the bristle plate and the light source unit on the head are combined with the body of the light irradiating toothbrush according to an embodiment of the present invention.
Figure 5:
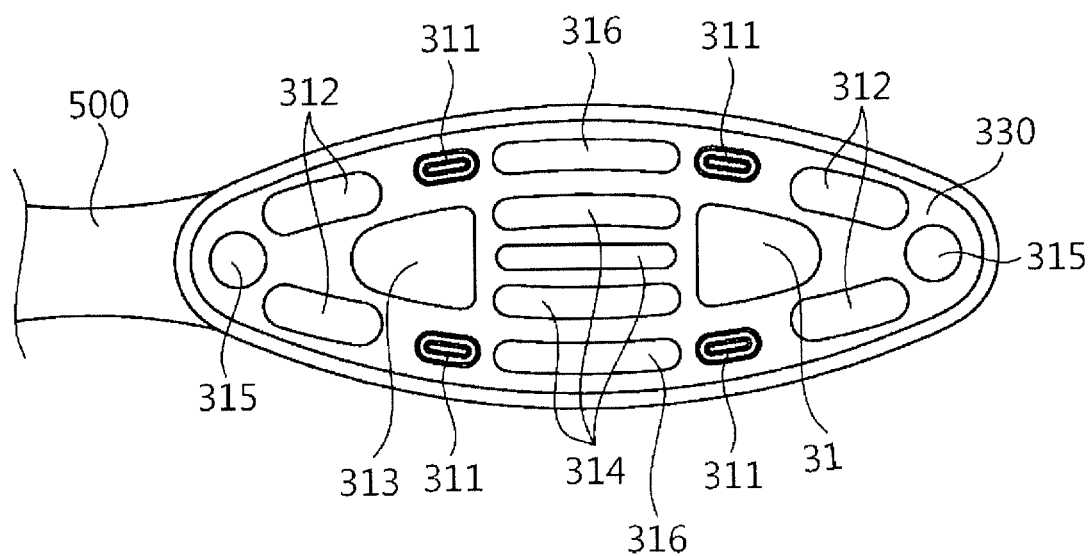
FIG. 5 is a plan view showing a case when the bristle plate on the head is combined with the body of the light irradiating toothbrush according to an embodiment of the present invention.

FIG. 3 is a view showing the positional relationship of the brushing bristles 310, the massaging bristles 311, the bristle plate 330, and the light source unit 320 on the head. FIG. 4 is a front view showing a case when the bristle plate 330 and the light source unit 320 on the head 300 are combined with the body 500 of the light irradiating toothbrush according to an embodiment of the present invention. FIG. 5 is a plan view showing a case when the bristle plate 330 on the head 300 is combined with the body 500 of the light irradiating toothbrush according to an embodiment of the present invention.

Hereinafter, the configuration of the head of the light irradiating toothbrush according to an embodiment of the present invention is described with reference to FIGS. 3 to 5.

The brushing bristles 310 include at least on waveguide and transmit light from light sources to the outside. The waveguide means a pipe that transmits light from a light source. The brushing bristle 310 can transmit light from a light source to a tooth of a user. The brushing bristles 310 using a waveguide can be made of an optical fiber.

The brushing bristles 310 may be coated with a metallic oxide catalyst or nano-metal. Coating with a metallic oxide catalyst and nano-metal is made by spraying them to the brushing bristles 310 or dipping the bristles therein. The metallic oxide catalyst is coated on the brushing bristles 310, using an alcohol liquid with a dispersed metallic oxide, and the nano-metal is coated on the brushing bristles 310, using a nitric acid nano-metal solution.

In some cases, the metallic oxide catalyst and the nano-metal both may be used, in which the brushing bristles 310 are coated with a mixture of an alcohol liquid containing dispersed metallic oxide with the nitric acid nano-metal solution.

The metallic oxide catalyst may be any one of $TiO_2$, $MnO_2$, and $BaTiO_3$, or a mixture of two of them, and basically it has a function of dissolving organic matters. In particular, $TiO_2$ is excellent in dissolution of organic matters and antibacterial function and $MnO_2$ is known as being excellent in deodorization.

The nano-metal may be any one of nano-silver (Ag), nano-copper (Cu), nano-white gold (Pt), and nano-gold (Au), or a mixture of two of them. The nano-metals have different functions and may be mixed for use purposes. The nano-metals generally have an antibacterial function, and particularly, nano-silver (Ag) and nano-copper (Cu) have an excellent anti-mold ability in comparison with other nano-metals, so the brushing bristles do not need sterilization.

The massaging bristles 311 may also be made of waveguides. The massaging bristles 311, which are used to massage the gums of a user, can transmit light from light sources and massage the gums, the inside of the cheek, or the tongue of a user. The massaging bristles 311 may be a bundle of optical fibers for transmitting light well. Alternatively, a bundle of optical fibers cannot have a diameter over a predetermined value, so the brushing bristles 311 may be manufactured by making a bundle of optical fiber in a set and inserting the bundle of optical fiber in the capsules of the brushing bristles 311. Similarly, the massaging bristles 311 may be manufactured by inserting a bundle of waveguides in the massaging bristles 311. The capsules of the massaging bristles 311 receives a bundle of optical fibers or a bundle of waveguides and may be made of a material that transmits light in order to transmit light traveling through the bundle of optical fibers or the bundle of waveguides to gums etc. The capsules 311 of the massaging bristles 311 may be covered with a bundle of optical fibers or a bundle of waveguides on the bristle plate 300 to form the massaging bristles 311.

One or both of the brushing bristles 310 and the massaging bristles 311 are disposed on the bristle plate 330 and a stepped portion may be formed at the bristle plate 330 so that the bristle plate can be detached from the head 300 of the body 500 for replacement. The bristle plate 330 may be made of a material that transmits light to transmit light from light sources to the outside.

Arrangement of the brushing bristles 310 is described with reference to FIG. 5. In the brushing bristles 310, brushing bristles 315 at both longitudinal end portions of the bristle plate are longer than the other brushing bristles 312, 313, 314, and 316 to transmit light well to back teeth. Alternatively, only one of the brushing bristles 315 at an end portion of the toothbrush may be made longest. The brushing bristles 312, 313, 314, and 316 may be arranged to corresponding to the arrangement of light sources. The massaging bristles 311 may be arranged at the corners of a virtual rectangle formed around the center of the elliptical bristle plate 330 to massage gums.

The light source unit 320 includes at least one light source. The light source may be a light emitting element such as an LED or a laser diode. The light sources radiate light with a specific wavelength. The light sources can radiate particularly blue or red light. The light sources can sterilize the inside of a user's mouth or bleach the teeth of a user. Alternatively, the light sources can achieve anti-inflammatory effect and stimulate collagen formation by radiating red light.

The light sources may be disposed on the second substrate 210. The second substrate 210 may be white to effectively reflect the light from the light sources to the brushing bristles 310. Light sources that radiate light with different wavelengths may be disposed on the second substrate 210. The light sources that radiate light with different wavelengths may be alternately arranged on the second substrate 210. For example, as shown in FIG. 4, sets composed of a first light source 321 that is a blue light source and a second light source 322 that is a red light source may be alternately arranged on the second substrate 210. The first light source 321 may be a blue light source and the second light source 322 may be a red light source. Sets of a sub-set having a plurality of blue light sources and a sub-set having a plurality of red light sources may be alternately arranged on the second substrate 210. The sub-sets may have the same number of light sources. Alternatively, it may be possible to make green light, white light, or light with other wavelengths by adding a blue or red light source, and it may be possible to generate a high frequency using a high frequency generator. The light sources may be arranged in the longitudinal direction of the second substrate 210. When a plurality of light sources is alternately arranged, the intensity of light can be improved by constructive interference of the light.

The light sources may be different in height, depending on the properties of the light that they radiate. This is described with reference to FIG. 4. The first light sources 321 and the second light sources 322 are alternately arranged on the second substrate 210. The first light source 321 may radiate light with a short wavelength, and in an embodiment, the light with a short wavelength may be blue light. The second light source 322 may radiate light with a long wavelength, and in an embodiment, the light with a long wavelength may be red light.

Considering that short-wavelength light disperses more than long-wavelength light, the first light sources 321 radiating short-wavelength light may be positioned closer to the brushing bristles 310 than the second light sources 322 radiating long-wavelength light so that the short-wavelength light travels a shorter distance to objects such as teeth or gums of a user, as compared with the long-wavelength light. The positions of the light sources may depend on the magnitudes of the wavelengths. The distances that the short-wavelength light and the long-wavelength light travel may be different in cases, so the positions of the light sources may be changed in accordance with the detailed configuration of the light irradiating toothbrush according to an embodiment of the present invention.

In more detail, in order to position the first light sources such that the short-wavelength light radiated from the first light sources travels a shorter distance to the brushing bristles, as compared with the long-wavelength light radiated from the second light sources and traveling to the brushing bristles, the first light sources radiating short-wavelength light may be positioned closer to the brushing bristles more than the second light sources radiating long-wavelength light, which can be achieved by making the first light sources higher than the second light sources. This means that the first light sources can be positioned vertically closer to the bristle plate than the second light sources on the second substrate. Accordingly, the first light sources can be higher than the second light sources. The first light sources and the second light sources may be configured to transmit light in only one direction, as seen in FIG. 4.

Figure 6:
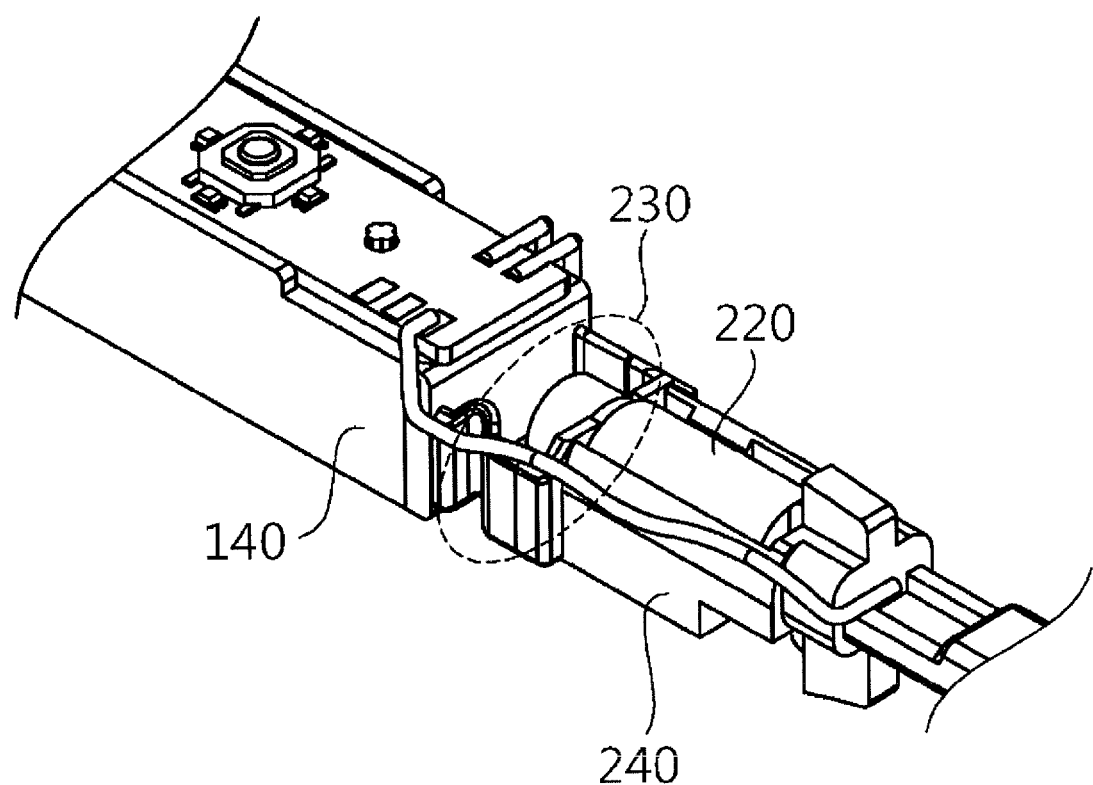
FIG. 6 is a perspective view showing the internal structure of a shank of the light irradiating toothbrush according to an embodiment of the present invention.

FIG. 6 shows the internal structure of the shank 200 of the light irradiating toothbrush according to an embodiment of the present invention. The vibrating motor 220 may be disposed at the grip 100 or the shank 200. In the light irradiating toothbrush according to an embodiment of the present invention, the vibrating motor 220 is disposed at the shank 200. This configuration is described in more detail with reference to FIG. 6. The vibrating motor 220 may be disposed inside the second housing 240.

The vibrating motor 220 applies a physical shock to the second substrate 210, using an elliptical rotor that rotates in the second housing 240, and the second substrate 210 applies a physical shock accordingly to the body 500, so the light irradiating toothbrush according to an embodiment of the present invention can be vibrated. Alternatively, it may be possible to apply a physical shock directly to the second housing 240 using the rotor and make the second housing 240 directly apply a physical shock to the body 500 or transmit vibration to the second substrate to vibrate the light irradiating toothbrush according to an embodiment of the present invention. Alternatively, it may be possible to make the rotor directly apply a physical shock to the body 500 to vibrate the light irradiating toothbrush according to an embodiment of the present invention. The rotor may have the shape of a half moon or the shape of an elliptical half moon.

The first housing 140 and the second housing 240 may be combined through the vibration attenuator 230. The vibration attenuator 230 can attenuate the intensity of the vibration that is transmitted from the second housing 240 to the first housing 140 by the vibrating motor 220. The vibration attenuator 230 may be made of a urethane material.

On the other hand, it is required to supply power to the electric motor, the operation light 120, the power switch 130, and the light source unit 320 in the light irradiating toothbrush according to the present invention, and to this end, the toothbrush may be connected to a home power by a DC adaptor or, when it is carried, it may be supplied with power from a battery or through a USB.

INDUSTRIAL APPLICABILITY

The present invention relates to an electric toothbrush including light sources radiating light and is available for the field of electric toothbrushes that can effectively suppresses oral bacteria.

The invention claimed is:

1. A light irradiating toothbrush comprising:
a grip;
a head connected to the grip;
a first substrate disposed in the grip; and
a second substrate disposed in the head;
wherein the head includes:
   a bristle plate disposed on the second substrate;
   brushing bristles made of at least one waveguide disposed on the bristle plate; and
   a light source unit disposed between the bristle plate and the second substrate and including a plurality of light sources radiating light through the at least one waveguide of the brushing bristles,
wherein the light source unit includes a first light source radiating short-wavelength light and a second light source radiating long-wavelength light and the short-wavelength light source and the long-wavelength light source are at different vertical distances under the bristle plate, in accordance with a magnitude of the wavelengths produced by the first light source and the second light source,
wherein the plurality of light sources is a set of light sources including a first sub-set that includes at least one first light source radiating short-wavelength light, and a second sub-set that includes at least one second light source radiating long-wavelength light,
wherein the plurality of light sources of the light source unit are alternatively arranged so that light of difference wavelengths give rise to constructive interference which strengthens an intensity of the irradiated light, and
wherein the first light source is positioned vertically closer to the bristle plate than the second light source.

2. The light irradiating toothbrush of claim 1, wherein the short-wavelength light is blue light and the long-wavelength light is red light.

3. The light irradiating toothbrush of claim 2, wherein the light irradiating toothbrush is supplied with power from a battery or through a USB.

4. The light irradiating toothbrush of claim 1, wherein the plurality of light sources are arranged in the longitudinal direction of the head.

5. The light irradiating toothbrush of claim 1, wherein the plurality of light sources are LEDs (Light-Emitting Diode) or laser diodes.

6. The light irradiating toothbrush of claim 1, wherein the brushing bristles are optical fibers.

7. The light irradiating toothbrush of claim 1, wherein the second substrate has a white color.

8. The light irradiating toothbrush of claim 1, further comprising a vibrating motor,
wherein the vibrating motor is connected to the second substrate and vibrates the second substrate.

9. The light irradiating toothbrush of claim 8, further comprising a vibration attenuator at a joint of the first substrate and the second substrate.

10. The light irradiating toothbrush of claim 9, wherein the vibration attenuator comprises a urethane material.

11. The light irradiating toothbrush of claim 1, wherein the head further includes massaging bristles made of waveguides.

12. The light irradiating toothbrush of claim 11, wherein the massaging bristles are formed by a bundle of a plurality of waveguides or a plurality of optical fibers.

13. The light irradiating toothbrush of claim 11, wherein the massaging bristles further include capsules covering the massaging bristles.

14. The light irradiating toothbrush of claim 11, wherein at least one of the brushing bristles and the massaging bristles is disposed on the bristle plate, and the bristle plate is detachably attached to the head.

15. The light irradiating toothbrush of claim 1, wherein the brushing bristles are coated with a metallic oxide catalyse or nano-metal.

16. The light irradiating toothbrush of claim 15, wherein the metallic oxide catalyst is any one of $TiO_2$, $MnO_2$, and $BaTiO_3$, or a mixture of two or more of $TiO_2$, $MnO_2$, and $BaTiO_3$.

17. The light irradiating toothbrush of claim 15, wherein the nano-metal is any one of nano-silver (Ag), nano-copper (Cu), nano-white gold (Pt), and nano-gold (Au), or a mixture of two of nano-silver (Ag), nano-copper (Cu), nano-white gold (Pt), and nano-gold (Au).

18. The light irradiating toothbrush of claim 1, wherein the light irradiating toothbrush is supplied with power from a battery or through a USB.

\* \* \* \* \*